United States Patent [19]

Felix et al.

[11] Patent Number: 5,792,098
[45] Date of Patent: Aug. 11, 1998

[54] SUCTION AND IRRIGATION HANDPIECE AND TIP WITH DETACHABLE TUBE

[75] Inventors: Augustus Felix, Providence; Roger Darois, Foster, both of R.I.

[73] Assignee: C. R. Bard, Inc., Murray Hill, N.J.

[21] Appl. No.: 666,759

[22] Filed: Jun. 19, 1996

[51] Int. Cl.⁶ .................................................. A61M 1/00
[52] U.S. Cl. ................................................ 604/27
[58] Field of Search ........................... 604/27, 35, 39, 604/40, 43, 173

[56] References Cited

U.S. PATENT DOCUMENTS

| | | |
|---|---|---|
| 1,987,907 | 1/1935 | Jenkins . |
| 3,065,749 | 11/1962 | Brass . |
| 3,889,675 | 6/1975 | Stewart . |
| 4,299,221 | 11/1981 | Phillips et al. . |
| 4,519,385 | 5/1985 | Atkinson et al. . |
| 4,692,140 | 9/1987 | Olson . |
| 4,790,812 | 12/1988 | Hawkins, Jr. et al. . |
| 4,861,332 | 8/1989 | Parisi . |
| 4,919,129 | 4/1990 | Weber, Jr. et al. . |
| 4,941,872 | 7/1990 | Felix et al. . |
| 5,147,292 | 9/1992 | Kullas et al. . |
| 5,230,704 | 7/1993 | Moberg et al. . |
| 5,269,750 | 12/1993 | Grulke et al. . |
| 5,310,406 | 5/1994 | Sharpe et al. . |
| 5,419,772 | 5/1995 | Teitz et al. . |
| 5,573,504 | 11/1996 | Dorsey, III ............................ 604/35 |

*Primary Examiner*—Manuel Mendez
*Attorney, Agent, or Firm*—Arthur Z. Bookstein

[57] ABSTRACT

An apparatus for irrigating a local irrigation site includes a suction/irrigation tip that is removably connected to a suction/irrigation handpiece. The tip includes a connector to detachably connect the tip to the handpiece, a suction tube detachably connected to the connector, and an irrigation tube permanently fastened to the connector. The tip may also have a securing clip to prevent the irrigation tube from bending during use, and a retaining finger to partially connect the tip to the handpiece.

22 Claims, 6 Drawing Sheets

SUCTION AND IRRIGATION HANDPIECE AND TIP WITH DETACHABLE TUBE

FIELD OF THE INVENTION

This invention relates generally to medical irrigation systems and, more particularly, to hand-held medical irrigation devices that use suction and irrigation tips.

BACKGROUND OF THE INVENTION

Suction and irrigation tips commonly are attached to the front (distal) end of hand-held suction and irrigation handpieces when localized irrigation is needed. Localized irrigation typically is needed during medical procedures such as, for example, orthopedic surgery, deep femoral surgery, and debridement procedures. Many specialized tips are therefore available that are designed specifically for one type of medical procedure. For example, tips used for deep femoral procedures typically are long and narrow so that they may extend entirely into the interior of the femur. Conversely, tips used to clean a joint during orthopedic surgery and tips used to clean a skin lesion during debridement procedures typically are much shorter and do not necessarily need to be as long and narrow.

One tip commonly used for the above noted procedures includes a suction tube that is connected to the suction lumen in the handpiece, and a separate irrigation tube that is connected to the irrigation lumen in the handpiece. The suction tube and irrigation tube are arranged in a side-by-side relationship, do not fluidly communicate, and permit either the irrigation tube or suction tube to be detached from the handpiece independently of the other tube. This tip therefore is most advantageous when used to irrigate a site within a region of the body having a small cross-sectional dimension, such as the interior of a femur. Although the femur is a relatively large bone, many people have a femur with a cross-sectional dimension that is not large enough to accept both a suction tube and an irrigation tube. In such a case, only the irrigation tube may be inserted into the femur when irrigation is needed, and only the suction tube may be inserted into the femur when suction is needed. Although this type of tip may be used to irrigate a femur with a small cross-sectional dimension, it nevertheless is inconvenient to use because it requires two separate tubes that must be separately attached to the handpiece.

U.S. Pat. No. 4,941,872 (Felix et al.) shows a similar tip having separate suction and irrigation tubes that are both detachably connected to a clip which "stiffens the assembly" of tubes. This tip also is disclosed as permitting either the irrigation tube or the suction tube to be detached from the handpiece independently of the other tube. Similar to the above noted tip, however, this tip requires that two separate tubes be separately attached to the handpiece fittings. Accordingly, this tip also is inconvenient to use.

Another tip commonly used for the above procedures includes a suction tube, an irrigation tube in a side-by-side relationship the suction tube, and a connector, permanently fastened to both of the tubes, that detachably connects the tip to the handpiece fittings. Since this tip is a one-piece structure, it connects to the handpiece fittings more conveniently than the prior mentioned tips. One problem with this type of tip, however, is that it cannot fit into a region, such as the interior of a femur, having a relatively small cross-sectional dimension.

It therefore is among the general objects of the invention to provide a suction and irrigation tip that may be conveniently attached to the handpiece fitting, and that permits either tube to be individually inserted into a region having a small cross-sectional dimension.

SUMMARY OF THE INVENTION

In accordance with one aspect of the invention, the connector in a detachable suction and irrigation tip having side-by-side suction and irrigation tubes is detachably connected to at least one of the tubes and permanently fastened to the other tube. The detachable tube extends through the connector so that the connector aligns the detachable tube with a lumen in the handpiece. The detachable tube connects directly with the handpiece to establish fluid communication. The permanently fastened other tube terminates on the connector which has a passage that fluidly connects the other tube to another lumen in the handpiece. The tip may have a slidable clip detachably connected to the one tube and permanently fastened to the other tube to prevent the tubes from bending during use. A shroud extends proximally from the connector and engages a fitting on the handpiece to prevent the tip from rotating when the detachable tube is removed. A securing finger may also extend proximally from the connector to engage a lip depending from the fitting to partially secure the tip to the handpiece.

The length of the suction and irrigation tubes may vary depending on the medical procedure with which the tip is used. When used in connection with femoral surgery, for example, the tubes should be long and narrow. Shorter tubes will suffice, however, when the tip is used in connection with debridement procedures or orthopedic surgery.

In accordance with one embodiment of the invention, the suction tube is detachably connected to the connector and the irrigation tube is permanently fastened to the connector. In another embodiment of the invention, the irrigation tube is detachably connected to the connector and the suction tube is permanently fastened to the connector. In a further embodiment, both tubes are detachably connected to the connector.

When in use, the handpiece irrigation lumen is connected to an irrigation source, the handpiece suction lumen is connected to a suction source, the tip is connected to the fitting at the distal end of the handpiece, and the tip is inserted into the irrigation region. No tubes need to be removed if the region has a cross-sectional dimension that can accept both the suction tube and the irrigation tube. If the region has a small cross-sectional dimension and irrigation only is needed, for example, a detachable suction tube can be removed and the permanently fastened irrigation tube can be inserted into the region to irrigate the site. After the site is irrigated, the irrigation tube and connector may be removed from the handpiece and the suction tube can be inserted directly into the handpiece fitting. The suction tube may then be inserted into the region to aspirate spent irrigation fluid and biological debris. The handpiece and tip may be discarded after use.

It is among the objects of the invention to provide a one-piece suction and irrigation tip that may easily and conveniently be connected to the suction and irrigation handpiece.

It is another object of the invention to provide a suction and irrigation tip that can access irrigation sites within regions of the body having a small cross-sectional dimension.

BRIEF DESCRIPTION OF THE DRAWINGS

The foregoing and other objects and advantages of the invention will be appreciated more fully from the following

Figure 1:
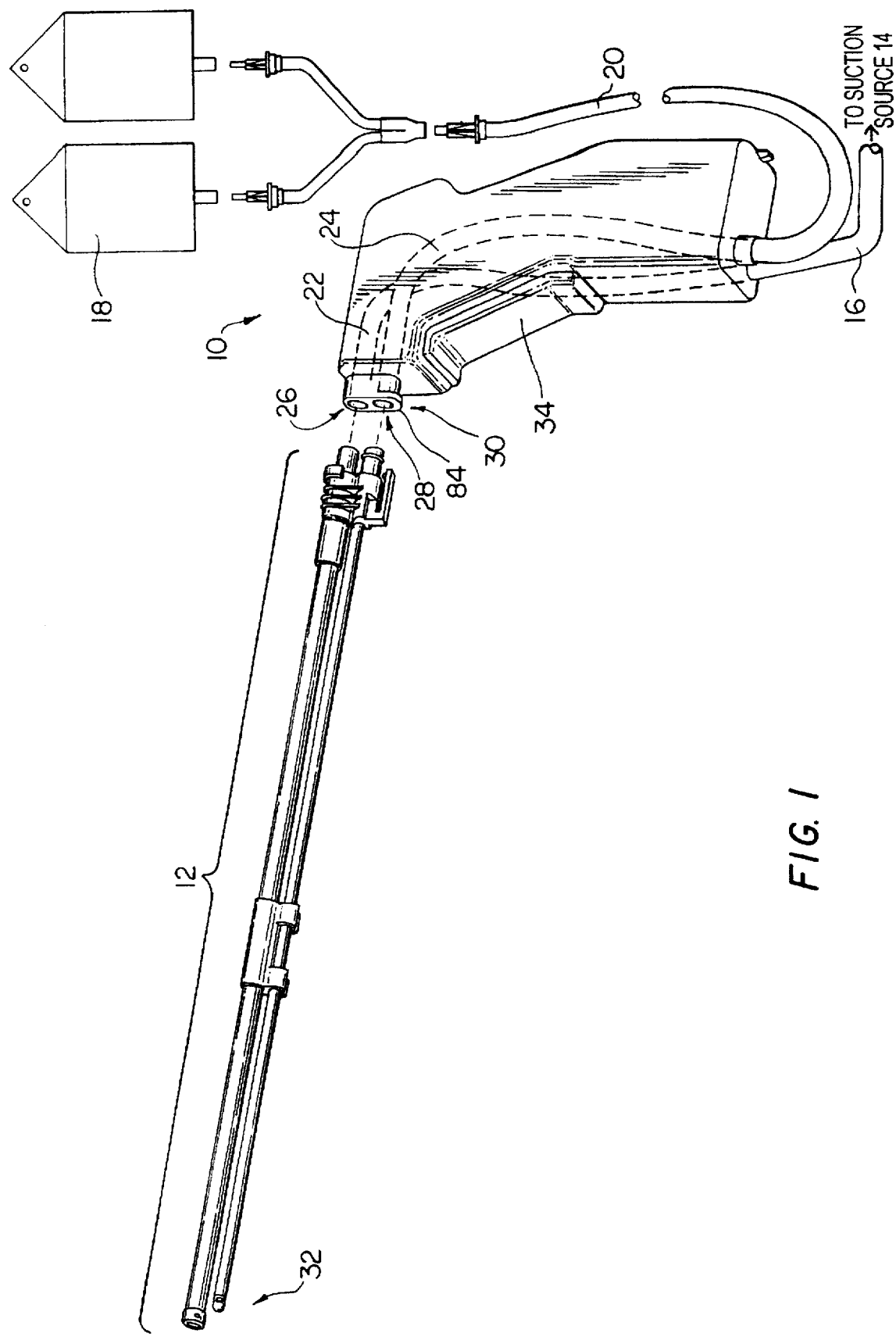
Figure 2:
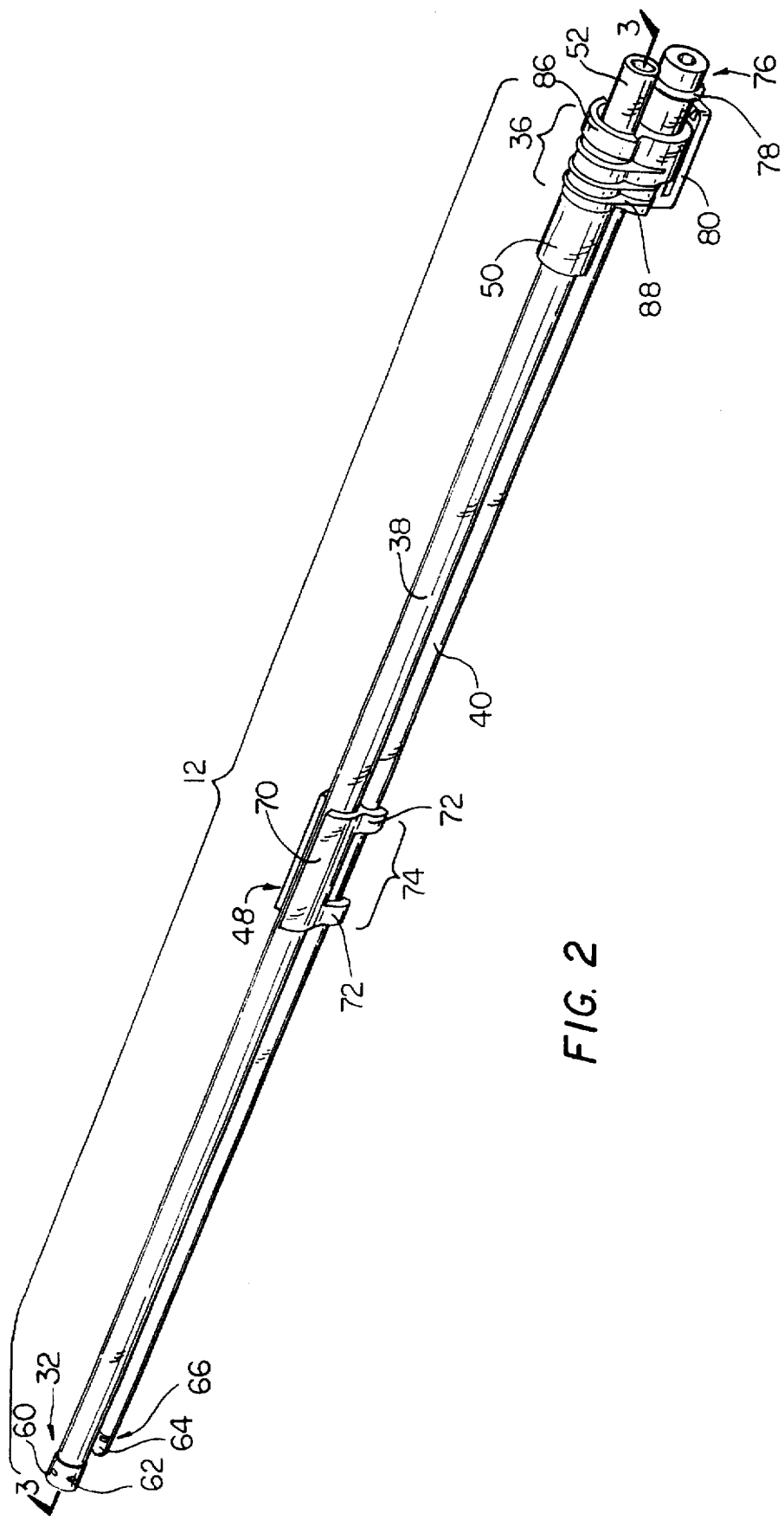
Figure 3:
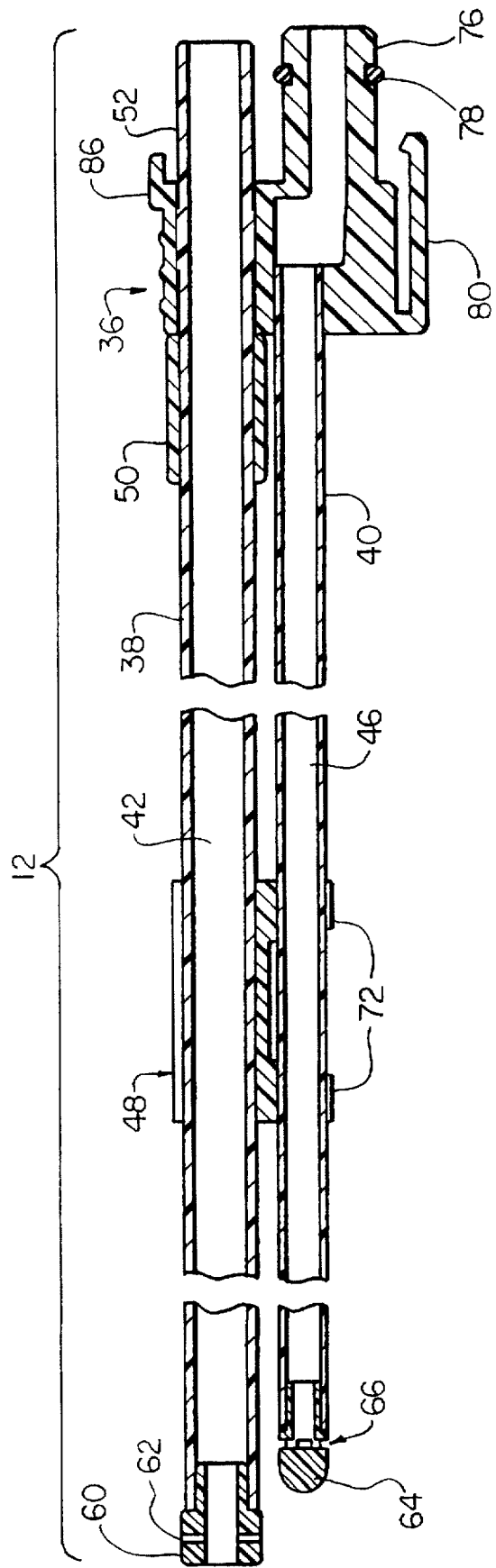
Figure 4:
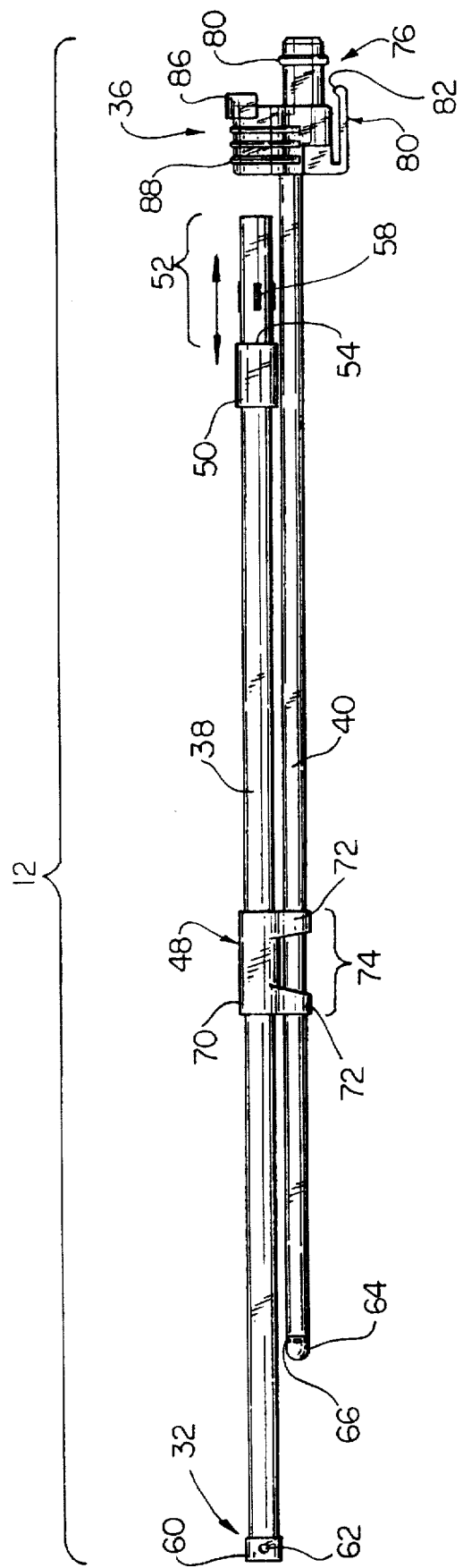
Figure 6:
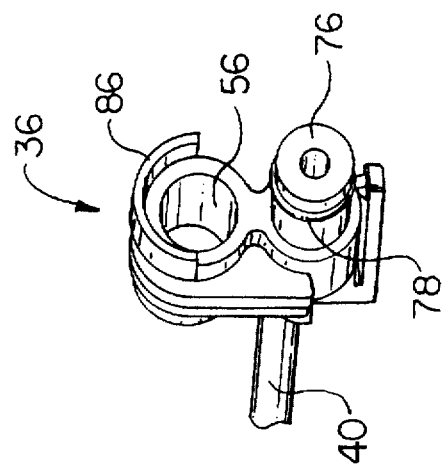
Figure 5:
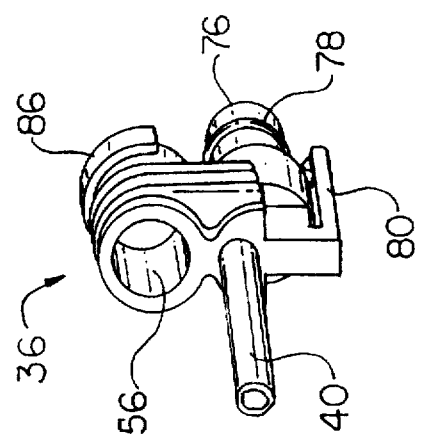
Figure 7:
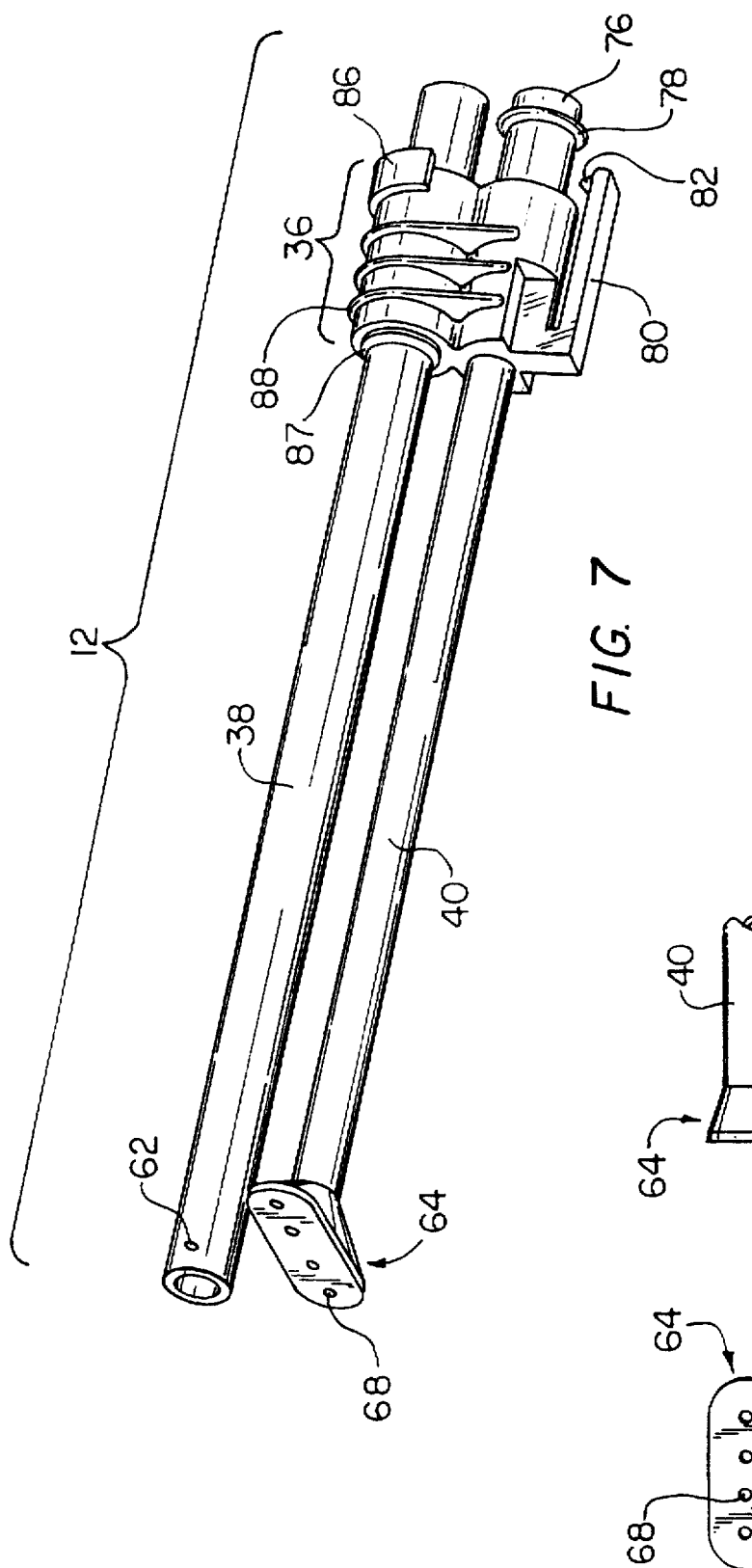
Figure 9:
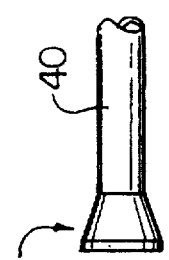
Figure 8:
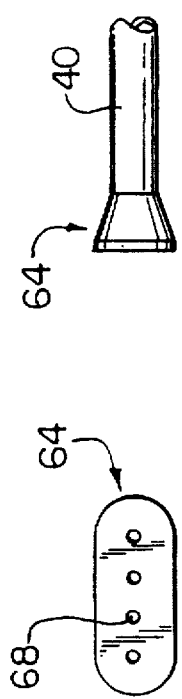

3 further description thereof with reference to the accompanying drawings wherein:

FIG. 1 is a perspective view of the preferred embodiment of the irrigation system in accordance with the invention;

FIG. 2 is a perspective view of the suction irrigation tip with the detachable tube connected to the connector;

FIG. 3 is a longitudinal cross section of the suction irrigation tip along line 3—3 of FIG. 2;

FIG. 4 is a side view of the suction irrigation tip with the detachable tube removed from the connector;

FIG. 5 is a front perspective view of the suction irrigation tip with the detachable tube removed;

FIG. 6 is a rear perspective view of the suction irrigation tip with the detachable tube removed;

FIG. 7 is an alternative embodiment of the suction irrigation tip;

FIG. 8 is a front view of the nozzle connected to the front end of the irrigation tube of the alternative embodiment; and FIG. 9 is a side view of the front end of the irrigation tube shown in FIG. 7.

DESCRIPTION OF THE ILLUSTRATIVE EMBODIMENT

FIG. 1 illustrates the main components of the suction irrigation system, which includes a conventional suction irrigation handpiece 10 and a suction irrigation tip 12 that is detachably connectable to the handpiece 10. The handpiece 10 is connected to a suction source 14 (e.g., wall suction) through flexible suction tubing 16, and to an irrigation source 18 (e.g., a saline bag) through flexible irrigation tubing 20. Irrigation liquid is pumped through the handpiece 10 and tip 12, to the irrigation site. Spent irrigation liquid and biological debris are aspirated through the tip 12 and handpiece 10, to a debris container (not shown).

The handpiece 10 may be a Simpulse Solo™ suction irrigation handpiece (available from C. R. Bard, Inc. of Murray Hill, N.J.) which has a self contained pump, battery, and motor (omitted for clarity), described in more detail in co-pending U.S. patent application Ser. No. 08/389,155 (assigned to C. R. Bard, Inc.). A suction lumen 22 and an irrigation lumen 24, both shown in phantom, extend through the entire length of the handpiece 10. The suction lumen 22 is connectable to a suction source 14 at a first end and terminates at a suction port 26 at a second end. Similarly, the irrigation lumen 24 is connectable to an irrigation source 18 at the first end and terminates at an irrigation port 28 at the second end. Both ports 26 and 28 are formed in a fitting 30 at the distal end of the handpiece 10.

In accordance with the principles of the invention, a detachable tip 12 can be connected to the handpiece 10. When the tip 12 is connected to the handpiece 10 and the handpiece 10 is energized, irrigation liquid passes through the irrigation port 28 and into the tip 12. The irrigation liquid is emitted in a pulsatile liquid stream from the distal end 32 of the tip 12 at a pulsating frequency that is controllable by a handpiece trigger 34. Suction also is applied to the site through the handpiece 10 and tip 12.

The preferred embodiment of the suction and irrigation tip 12, illustrated in FIGS. 2–6, may be made from a clear plastic material. The tip 12 includes a rigid tip connector 36 to detachably connect the tip 12 to the handpiece fitting 30, an elongated, rigid suction tube 38 detachably connected to the tip connector 36 (FIG. 4), and an elongated, flexible irrigation tube 40 permanently fastened to the tip connector 36. The suction tube 38 defines a suction lumen 42 having

4 a uniform inner diameter (e.g., about 0.25 inches) that directs spent irrigation liquid and biological debris from the irrigation site to the handpiece suction port 26. Similarly, the irrigation tube 40 defines a tip irrigation lumen 46 having a uniform inner diameter (e.g., about 0.125 inches) that directs irrigation liquid from the handpiece irrigation port 28 to the site. A retaining clip 48 (discussed in detail below) may be slidably fastened to the suction tube 38 and detachably connected to the irrigation tube 40 to prevent the flexible irrigation tube 40 from bending during use.

A collar 50 encircling a portion of the suction tube 38 defines a connection segment 52 that extends from a proximal shoulder 54 of the collar 50 to the proximal end of the suction tube 38. The connection segment 52 is slidably received by a through hole 56 in the connector 36 (discussed in more detail below) having an inner diameter that is smaller than the outer diameter of the collar 50. The connection segment 52 may include a plurality of ridges 58 that enlarge the outer diameter of the suction tube 38 in that region. This enlarged diameter adds a mechanical resistance to the suction tube 38 when it is slid into and out of the connector 36 through hole 56 to frictionally secure the suction tube 38 within the through hole 56. A cylindrical insert 60 having a smaller inner diameter than the suction tube 38 may be fastened to the distal end of the suction tube 38 to prevent larger pieces of debris from being drawn into the suction tube 38. This reduces the possibility of the suction tube 38 becoming clogged with larger pieces of biological debris drawn from the irrigation site. One or more suction relief holes 62 may also be formed near the distal end of the suction tube 38 or in the side surface of the cylindrical insert 60 to prevent trauma to an irrigation surface if the open end of the tip suction lumen 42 becomes occluded by that surface.

The proximal end of the irrigation tube 40 may be permanently fastened to the connector 36 by means of a securing adhesive. An irrigation nozzle 64 may be permanently fastened to the distal end of the irrigation tube 40 to provide a specialized spray pattern to the irrigation liquid emitted from the irrigation tube 40. The nozzle 64 may be any nozzle 64 known in the art that is useful for the for the purposes with which the tip 12 is being used. For example, the nozzle 64 shown in FIGS. 1–4 is useful in irrigating the interior of a femur since it has a closed end and a side surface with one or more irrigation holes 66. When using this nozzle 64, irrigation liquid is emitted radially from the irrigation tube 40 as the tip 12 is moved longitudinally within the femur. As a further example, the nozzle 64 shown in FIGS. 7–9 (discussed in more detail below) has four longitudinal holes 68 and is useful for debridement procedures and orthopedic surgical irrigation.

As noted above, the irrigation tube 40 of the preferred embodiment may undesirably bend during use because it is long and flexible. This bending can cause the inner diameter of the irrigation tube 40 to be non-uniform, thus impeding the flow of irrigation liquid from the irrigation tube 40. Accordingly, the suction tube 38 and the irrigation tube 40 also are connected by the retaining clip 48 to prevent the irrigation tube 40 from bending during use. The clip 48 is formed from a plastic material having an upper circular collar 70 and an integral pair of downwardly extending arcuate fingers 72. The circular collar 70 slidably mounts on the suction tube 38 and the fingers 72 extend downwardly to define a receptive clip 74 for the irrigation tube 40. The fingers 72 are open at the bottom diameter of the irrigation tube 40 to detachably connect to the irrigation tube 40 in a snap-fit. The detachable retaining clip 48 permits either of the irrigation tube 40 or suction tube 38 to be detached independently from of the other tube.

The connector 36 forms the through hole 56 (mentioned above and shown in detail in FIGS. 5 and 6) that slidably receives the connection segment 52 of the suction tube 38 and aligns the suction tube 38 with the handpiece suction lumen 22. As noted above, the diameter of the through hole 56 should approximate the outer diameter of the suction tube 38 (defined in part by the ridges 58 on the connection segment 52) to frictionally secure the suction tube 38 to the connector 36. Since the collar 50 has a larger outer diameter than the inner diameter of the through hole 56, the suction tube 38 can slide through the through hole 56 to the proximal shoulder 54 only. An irrigation connector plug 76, extending proximally from the tip connector 36, detachably connects to the irrigation port 28 in the handpiece 10 and directs irrigation liquid from the irrigation port 28 to the tip irrigation lumen 42. A sealing O-ring 78 may encircle the irrigation connector plug 76 to fluidly seal the connection between the irrigation port 28 and the irrigation connector 76. A securing finger 80, extending proximally from the connector 36, partially connects the tip 12 to the handpiece 10 by means of a proximal tooth 82 that engages a lip 84 extending downwardly from the fitting 30. The outer surface of the connector 36 may have ridges 88 that facilitate gripping of the connector 36 when the tip 12 is attached to and removed from the handpiece fitting 30.

The connector 36 may also have a proximally extending semi-circular shroud 86 that prevents the tip 12 from rotating about the irrigation connector plug 76 when the suction tube 38 is not connected to the tip 12. To that end, the shroud 86 has an inner dimension approximating the outer top dimension of the fitting 30. When the tip is connected to the fitting 30, the shroud 86 surrounds the outer diameter of the fitting 30 which, in combination with the connection between the irrigation connector plug 76 and the fitting 30 at the irrigation port 28, prevents the tip from rotating about the irrigation connection plug 76.

In the preferred embodiment, for example, the outer diameter of the suction tube 38 may be about 0.28 inches and the inner diameter of the through hole 56 may be about 0.31 inches to loosely receive the suction tube 38. The ridges 58 on the connection segment 52 may extend radially about 0.02–0.03 inches to frictionally secure the suction tube 38 within the through hole 56. The outer diameter of the collar 50 may be about 0.41 inches (i.e. 0.10 inches larger than the inner diameter of the through hole 56) to prevent the suction tube 38 from being slid entirely through the through hole 56. The suction tube 38 (including the cylindrical insert 60) may have a total length of about 12.625 inches and may extend about 11.625 inches from the proximal shoulder 54 on the collar 50. The irrigation tube 40 (including the nozzle 64) may extend about 11.25 inches from the tip connector 36 and thus be about 0.375 inches shorter than the suction tube 38. It should be understood, however, that these dimensions are merely exemplary and are in no way intended to limit the scope of the invention.

FIGS. 7–9 show an alternative embodiment of the suction and irrigation tip 12 which may be useful in debridement procedures or orthopedic surgery. Unlike the preferred embodiment, this embodiment of the tip 12 does not require the retaining clip 48 to prevent the irrigation tube 40 from bending since the irrigation tube 40 is made from a hard plastic and is substantially shorter than the preferred embodiment. In addition, the nozzle 64 fastened to the distal end of this tip 12 (commonly referred to as a "showerhead" nozzle 64) has four longitudinal holes 68 that direct irrigation liquid longitudinally from the irrigation tube 40. The suction tube 38 on this embodiment furthermore does not have the cylindrical insert 60 since the suction tube 38 is much shorter (e.g., a total length of about 4.25 inches, but extending only about 3.0 inches from the connector 36) than the suction tube 38 on the preferred embodiment and thus, is less likely to clog. The collar 50 on the preferred embodiment also may be omitted in favor of an annular ridge 87 encircling the suction tube 38. Like the preferred embodiment, the inner diameter of the suction and irrigation tubes 38 and 40 in the alternative embodiment is uniform from the distal end to the proximal end of the tip 12.

In another alternative embodiment, the irrigation tube 40 may be detachably connected to the connector 36 and the suction tube 38 may be permanently fastened to the connector 36. In yet another alternative embodiment, both the suction tube 38 and the irrigation tubes 38 and 40 may be detachably connected to the connector 36. In still another alternative embodiment, either or both of the suction tube 38 and the irrigation tube 40 are detachably connected to the connector 36 and neither of the tubes 38 or 40 connect directly to the handpiece suction lumen 22 or the handpiece irrigation lumen 24. To that end, the connector 36 in this embodiment has both a suction plug that fluidly connects the suction tube 38 to the handpiece suction lumen 22, and the irrigation plug 76 that fluidly connects the irrigation tube 40 to the handpiece irrigation lumen 24.

Prior to use, the tip connector 36 is inserted into the handpiece fitting 30, the flexible suction tubing 16 is connected to the handpiece suction lumen 22, and the flexible irrigation tubing 20 is connected to the handpiece irrigation lumen 24. When used to irrigate a site within a region having a small-cross sectional dimension, such as the interior of a femur, the physician first should attempt to insert both the suction and irrigation tubes 38 and 40 into that region. If the cross-sectional dimension is too small to accept both tubes, then the suction tube 38 may be removed and the irrigation tube 40 only may be inserted. After the site is irrigated, the irrigation tube 40 and connector 36 may be removed and the suction tube 38 may be connected to the suction port 26 at the fitting 30 and inserted into the irrigation region. The tip 12 and handpiece 10 are discarded after use.

The above process similarly is used to irrigate an externally traumatized region of the body, such as a bed sore. If irrigation only is desired, the suction tube 38 may be removed to leave only the irrigation tube 40 connected. If suction only is desired, the irrigation tube 40 and connector 36 may be removed and the suction tube 38 may be inserted into the suction port 26 at the fitting 30. The tip 12 and handpiece 10 are discarded after use.

It should be understood that the foregoing description of the invention is intended merely to be illustrative thereof and that other modifications and embodiments may be apparent to those skilled in the art without departing from its spirit.

Having thus described the invention, what we desire to claim and secure by letters patent is:

1. A suction and irrigation tip for use with a suction and irrigation handpiece having suction and irrigation lumens, the tip comprising:

an irrigation tube;

a suction tube; and a connector detachably connectible to the handpiece and to at least one of the suction and irrigation tubes to enable one of the tubes to be detached from the connector while the other tube remains connected, by the connector, to the handpiece;

said at least one of the tubes that is detachable from the connector having an end that is functionally connectible to a lumen of the handpiece independently of the connector.

2. The suction and irrigation tip as defined by claim 1 wherein the one tube extends through the connector to connect directly with the handpiece.

3. The suction and irrigation tip as defined by claim 1 wherein the one tube has a collar that defines a connection segment and the connector forms a through hole, the connection segment being slidably received by the through hole.

4. The suction and irrigation tip as defined by claim 3 wherein the outer surface of the connection segment includes a ridge.

5. The suction and irrigation tip as defined by claim 1 further including a securing finger extending from the connector to secure the tip to the handpiece.

6. The suction and irrigation tip as defined by claim 1 wherein the one tube is the irrigation tube connectible to the irrigation lumen in the handpiece, and the other tube is the suction tube.

7. The suction and irrigation tip as defined by claim 1 wherein the one tube is the suction tube connectible to the suction lumen in the handpiece, and the other tube is the irrigation tube.

8. The suction and irrigation tip as defined by claim 1 further including a shroud extending from the connector to couple with the handpiece to prevent the tip from rotating relative to the handpiece.

9. The suction and irrigation tip as defined by claim 1 further including a retaining clip connected to both the irrigation tube and the suction tube.

10. A system for irrigating a site comprising:
a handpiece including a nozzle, a suction lumen, and an irrigation lumen, the suction lumen and irrigation lumen in fluid communication with the nozzle;
a tip detachably connected to the nozzle, the tip comprising:
an irrigation tube;
a suction tube; and
a connector detachably connected to the handpiece, one of the suction and irrigation tubes being detachably connected to the connector and the other of the suction and irrigation tubes being permanently fastened to the connector so that when the connector is connected to the handpiece, the suction tube is in fluid communication with the suction lumen and the irrigation tube is in fluid communication with the irrigation lumen, the one of the suction and irrigation tubes being detachable from the connector when the other tube is connected in fluid communication to the handpiece.

11. The system as defined by claim 10 wherein the one tube extends through the connector to connect directly with the handpiece.

12. The system as defined by claim 10 wherein the one tube has a collar that defines a connection segment and the connector forms a through hole, the connection segment being slidably received by the through hole.

13. The system as defined by claim 12 wherein the outer surface of the connection segment includes a ridge.

14. The system as defined by claim 10 further including a securing finger extending from the connector to secure the tip to the handpiece.

15. The system as defined by claim 10 wherein the one tube is the irrigation tube and the other tube is the suction tube.

16. The system as defined by claim 10 wherein the one tube is the suction tube and the other tube is the irrigation tube.

17. The system as defined by claim 10 further including a shroud extending from the connector to couple with the handpiece nozzle to prevent the tip from rotating relative to the handpiece.

18. The system as defined by claim 10 further including a retaining clip connected to both the irrigation tube and the suction tube.

19. A suction and irrigation tip for use with a suction and irrigation handpiece having suction and irrigation lumens, the tip comprising:
an irrigation tube;
a suction tube; and
a connector detachably connected to the handpiece, one of the suction and irrigation tubes being detachably connected to the conncetor and the other of the suction and irrigation tubes being connected to the connector so that when the connector is connected to the handpiece, the suction tube is in fluid communication with the suction lumen and the irrigation tube is in fluid communication with the irrigation lumens,
the tip having a first cross-sectional dimension when the suction tube and irrigation tube are connected to the connector,
the tip having a second cross-sectional dimension when the one of the suction and irrigation tubes is detached;
the second cross-sectional dimension being smaller than the first cross-sectional dimension.

20. The suction and irrigation tip as defined by claim 19 wherein the at least one of the suction and irrigation tubes extends through the connector to connect directly with the handpiece.

21. The suction and irrigation tip as defined by claim 19 wherein the connector includes an irrigation plug that fluidly connects the irrigation tube to the irrigation lumen in the handpiece.

22. The suction and irrigation tip as defined by claim 19 wherein the other of the suction and irrigation tubes is detachably connected to the connector.

* * * * *